(12) United States Patent
Yang et al.

(10) Patent No.: US 7,799,747 B2
(45) Date of Patent: *Sep. 21, 2010

(54) METHOD OF REDUCING SURFACTANT DAMAGE USING COMPOSITIONS COMPRISING BENEFIT AGENTS OF DEFINED HIGH POLARITY

(75) Inventors: Lin Yang, Woodbridge, CT (US); Martin Vethamuthu, Southbury, CT (US); Carol Vincent, Trumbull, CT (US); Alexander Lips, New Canaan, CT (US); Kavssery Parameswaran Ananthapadmanabhan, Woodbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 890 days.

This patent is subject to a terminal disclaimer.

(21) Appl. No.: 11/291,596

(22) Filed: Dec. 1, 2005

(65) Prior Publication Data

US 2007/0129270 A1    Jun. 7, 2007

(51) Int. Cl.
*A61K 7/00* (2006.01)
(52) U.S. Cl. .................. 510/130; 510/156; 510/417; 510/424; 510/426; 510/428
(58) Field of Classification Search .............. None
See application file for complete search history.

(56) References Cited

U.S. PATENT DOCUMENTS

2008/0004192 A1 *  1/2008   Vedantam et al. ............ 510/122

* cited by examiner

*Primary Examiner*—Necholus Ogden, Jr.
(74) *Attorney, Agent, or Firm*—Ronald A. Koatz

(57) ABSTRACT

The invention provides a method of reducing surfactant damage in compositions comprising at least one surfactant and at least one benefit agent. The reduction in damage is measurable by decrease in number of protein binding sites in presence versus absence of benefit agent, or when benefit agent has solubility outside a defined range. The invention further relates to compositions comprising said surfactants and benefit agent(s) having reduced surfactant damage.

2 Claims, 6 Drawing Sheets

Figure 6 shows the comparison between the in-vitro surfactant binding to protein to in-vivo skin irritation.

METHOD OF REDUCING SURFACTANT DAMAGE USING COMPOSITIONS COMPRISING BENEFIT AGENTS OF DEFINED HIGH POLARITY

FIELD OF THE INVENTION

The present invention relates to a method of significantly reducing surfactant damage (e.g., to skin or other protein-containing substrate) by utilizing compositions comprising benefit agents (e.g., oils, solvents) within a defined high polarity window (wherein polarity is measured using "Hansen Solubility Parameter" of the benefit agent). The invention further relates to compositions, particularly compositions effective in reducing skin/protein damage, comprising benefit agents/oils falling within the defined polarity window. In another embodiment, the invention relates to a method of selecting benefit agents/oils or a class of benefit agents/oils which are best suited for reducing surfactant damage in surfactant containing compositions using knowledge of Hansen solubility.

BRIEF SUMMARY OF THE INVENTION

It is well known that surfactant/cleanser can be harsh and damaging to the skin. Generally, it is believed this occurs at least in part, because surfactant binds to proteins found in the skin and thereby interferes with the role of the protein (e.g., in maintaining healthy skin).

It is also well known to utilize personal care compositions comprising benefit agents, such as oils. Oils are thought to provide an occlusion barrier and to help alleviate skin dryness by, for example, reducing water loss from the skin barrier.

Unexpectedly, applicants have now found that use of benefit agent in surfactant containing personal care compositions (e.g., personal care liquids, bars, etc.), particularly benefit agent falling within specific polarity parameters (i.e., the polarity of the benefit agent or combination of benefit agents), leads to reduced damage of skin/substrate normally caused by the surfactant in such compositions. While not wishing to be bound by theory, it is believed that benefit agents falling within the defined polarity profiles act to inhibit the process of protein denaturing by interacting with the protein, thereby effectively blocking the binding site on the protein molecule that is available for surfactant binding. It is this binding of surfactant to protein which is believed largely responsible for the harmful impact of surfactant on skin.

In one embodiment, the invention further relates to a method of selecting benefit agents/oils suitable for reducing surfactant damage using knowledge of Hansen solubility parameters.

The following references are noted: U.S. Pat. No. 6,699,824 to Dawson et al.; EP 1 051 468 (assigned to Unilever); U.S. Pat. No. 6,380,150 to Toussaint et al.; JP 2004/203848 (assigned to Lion Corp); EP 0 912 666 (assigned to Colgate); and WO 96/37594 (assigned to P&G).

None of the noted references teaches or suggests a method of reducing surfactant damage to skin or other substrate using benefit agents (e.g., oils, solvents) having a defined polarity or a method of selecting benefit agents or a class of benefit agents suitable for reducing such damage.

BRIEF DESCRIPTION OF THE INVENTION

In one embodiment, the present invention relates to a method of reducing surfactant damage (e.g., reducing surfactant binding to skin proteins) which comprises using surfactant-containing compositions (preferably, but not necessarily, liquid compositions) comprising benefit agent or combination of benefit agents having high polarity (within a defined polarity window). The polarity of a benefit agent can in turn be expressed as a function of the Hansen solubility parameter of the benefit agent.

In a preferred embodiment of the first embodiment, the invention relates to a method of reducing surfactant damage in a composition comprising surfactant or surfactants, preferably comprising at least one anionic surfactant (generally anionic surfactants are harsher than other surfactants on skin), wherein said method comprises using, in addition to the surfactant or surfactants, a benefit agent(s) with Hansen solubility parameter between about 16.5 and 37 (see examples), preferably 17 and 30, more preferably between 19 and 27.

In a second embodiment of the invention, the invention comprises a method of selecting benefit agent to be used to reduce surfactant damage in a composition comprising at least one surfactant and benefit agent, wherein said process comprises (1) determining Hansen solubility parameters (HSP) of the benefit agent (e.g., by calculating the HSP using molecular modeling software, such as ChemSW (version 3.33), which uses an empirical group contribution model to calculate HSP based on known chemical structure); and (2) selecting said benefit agent(s) having HSP of between 16.5 and 37 alone or in combination, preferably having HSP of between 17 and 30, more preferably 19 and 27.

In a third embodiment, the invention relates to compositions comprising surfactant and a benefit agent or combination of benefit agents having HSP from 16.5 to 37. Such composition has reduced surfactant damage (e.g., at least 5% fewer binding sites) relative to composition with same type and amount of surfactant(s) comprising benefit agent(s) having HSP below 16.5 or above 37 or having no benefit agent.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
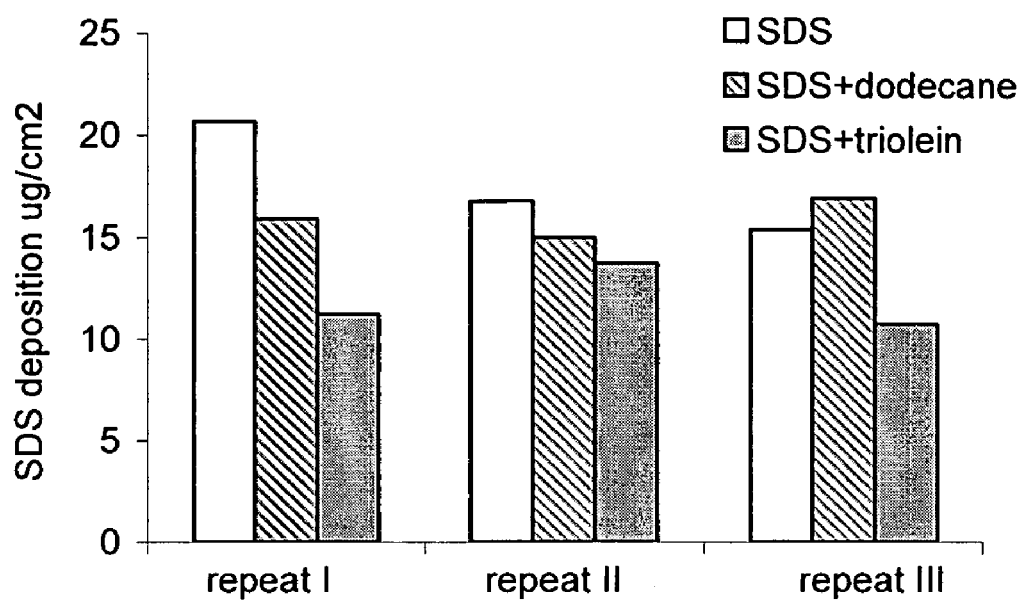
FIG. 1 is a graph of surfactant deposition (i.e., deposition of anionic surfactant sodium dodecyl sulfate, or SDS), measured in micrograms/cm$^2$ (analyzed by HPLC method) when measured alone and when measured with various benefit agents (oils, solvents, etc.). As noted, when measured in combination with triolein, a high polarity oil having an HSP within the range defined by the invention (HSP of 23.77) deposition decreases. This is a signal of less surfactant binding. By contrast, when measured in combination with dodecane (relatively non-polar oil of HSP 16.02), deposition was about the same or higher (more binding).

The present invention relates to the fundamental observation that, when a surfactant system which normally causes damage to skin or other substrate (e.g., by causing denaturing of protein) is used in combination with benefit agent or agents of a defined polarity, the surfactant damage (measured by the number of surfactant molecular binding sites binded per protein molecule) caused by the surfactant can be reduced.

In one embodiment of the invention, the invention relates to a method of reducing surfactant damage (measurable, for example, by reduction in number of surfactant binding per protein molecule) of at least about 5% compared to number of sites binded using surfactant(s) and no benefit agent or benefit agent outside polarity window, wherein said method comprises, in compositions comprising at least one surfactant and at least one benefit agent, selecting a benefit agent or combination of benefit agents having high polarity. Polarity of benefit agents so used can be expressed as a function of the HSP. In another embodiment, the invention relates to a method of selecting benefit agent(s) suitable for reducing the surfactant damage.

Surfactant

Preferably, although not necessarily, the at least one surfactant should be an anionic surfactant and, if a mixture of surfactants is used, at least one of said mixture should be an anionic surfactant.

Surfactant(s), when used in a fully formulated composition, may comprise from 2% to 90% of the composition, depending on whether the surfactants are formulated as part of a bar composition, liquid composition, cream, etc.

For example, if part of a rinse-off liquid cleanser composition, surfactant or surfactants may comprise 2 to 75% of a surfactant selected from the group consisting of anionic, nonionic, amphoteric/zwitterionic, cationic surfactant and mixtures thereof.

Among suitable anionic actives which may be used are the alkyl ether sulfates, acyl isethionates, alkyl ether sulfonates, sarcosinates, sulfosuccinates, taurates and combinations thereof. Among suitable amphoteric actives may be included alkylbetaines, amidopropyl betaines, amidopropyl sultaines and combinations thereof.

Alkyl ether sulfates of the present invention may be of the general formula

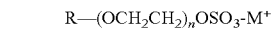

wherein R ranges from $C_8$-$C_{20}$ alkyl, preferably $C_{12}$-$C_{15}$ alkyl, n is an integer from 1 to 40, preferably from 2 to 9, optimally about 3, and $M^+$ is a sodium, potassium, ammonium or triethanolammonium cation.

Typical commercial co-actives of this variety are listed in the Table below:

| Trademark | Chemical Name | Physical Form | Manufacturer |
|---|---|---|---|
| Steol CS 330 | Sodium Laureth Sulfate | Liquid | Stepan |
| Standopol ES-3 | Sodium Laureth Sulfate | Liquid | Henkel |
| Alkasurf ES-60 | Sodium Laureth Sulfate | Paste | Alkaril |
| Cycloryl TD | TEA Laureth Sulfate | Paste | Cyclo |
| Standopol 125-E | Sodium Laureth-12 Sulfate | Liquid | Henkel |
| Cedepal TD407MF | Sodium Trideceth Sulfate | Paste | Miranol |
| Standopol EA-2 | Ammonium Laureth Sulfate | Liquid | Henkel |

Alkyl ether sulfonates may also be employed for the present invention. Illustrative of this category is a commercial product known as Avenel S-150 commonly known as a sodium $C_{12}$-$C_{15}$ Pareth-15 sulfonate.

Another active type suitable for use in the present invention is that of the sulfosuccinates. This category is best represented by the monoalkyl sulfosuccinates having the formula $R_2OCCH_2CH(SO_3XNa^+)COOXM^+$; and amido-MEA sulfosuccinates of the formula: $RCONHCH_2CH_2O_2CCH_2CH(SO_3XM^+)COOXM^+$; wherein R ranges from $C_8$-$C_{20}$ alkyl, preferably $C_{12}$-$C_{15}$ alkyl and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Emcol 4400-1 | Disodium Lauryl Sulfosuccinate | Solid | Witco |
| Witco C5690 | Disodium Cocoamido MEA Sulfosuccinate | Liquid | Witco |
| McIntyre Mackanate CM40F | Disodium Cocoamido MEA Sulfosuccinate | Liquid | McIntyre |
| Schercopol CMSNa | Disodium Cocoamido MEA Sulfosuccinate | Liquid | Scher |
| Emcol 4100M | Disodium Myristamido MEA Sulfosuccinate | Paste | Witco |
| Schercopol | Disodium Oleamido MEA | Liquid | Scher |
| Varsulf S13333 | Disodium Ricionoleamido MEA Sulfosuccinate | Solid | Scherex |

Sarcosinates may also be useful in the present invention as a co-active. This category is indicated by the general formula $RCON(CH_3)CH_2CO_2XM^+$, wherein R ranges from $C_8$-$C_{20}$ alkyl, preferably $C_{12}$-$C_{15}$ alkyl and $M^+$ is a sodium, potassium ammonium or triethanolammonium cation. Typical commercial products representative of these co-actives are those listed in the Table below:

| Trademark | Chemical Name | Physical Form | Manufacturer |
|---|---|---|---|
| Hamposyl L-95 | Sodium Lauroyl Sarcosinate | Solid | W. R. Grace |
| Hamposyl TOC-30 | TEA Cocoyl/Sarcosinate | Liquid | W. R. Grace |

Taurates may also be employed in the present invention as co-actives. These materials are generally identified by the formula $RCONR'CH_2CH_2SO_3XM^+$, wherein R ranges from $C_8$-$C_{20}$ alkyl, preferably $C_{12}$-$C_{15}$ alkyl, R' ranges from $C_1$-$C_4$ alkyl, and $M^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CH_2CO_2XM^+$, amidopropyl betaines of the formula $RCONHCH_2CH_2CH_2N^+(CH_3)_2CH_2CO_2XM^+$, and amidopropyl sultaines of the formula $RCONHCH_2CH_2N^+(CH_3)_2CH_2SO_3XM^+$ wherein R ranges from $C_8$-$C_{20}$ alkyl, preferably $C_{12}$-$C_{15}$ alkyl, and $M^+$ is a sodium, potassium, ammonium or triethanolammonium cation. Typical commercial products representative of these co-actives are found in the Table below:

| Trademark | Chemical Name | Physical Form | Manufacturer |
|---|---|---|---|
| Tegobetaine F | Cocamidopropyl Betaine | Liquid | Goldschmidt |
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamidopropyl Betaine | Liquid | Lonza |
| Velvetex OLB-50 | Oleyl Betaine | Paste | Henkel |

Within the broad category of liquid actives, the most effective are the alkyl sulfates, alkyl ether sulfates, alkyl ether sulfonates, sulfosuccinates, and amidopropyl betaines.

Another preferred surfactant is an acyl isethionate having the formula

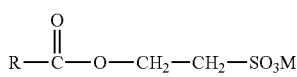

in which R denotes a linear or branched alkyl group and M denotes an alkali metal or alkaline earth metal or an amine.

Another surfactant which may be used are the monoalkyl or dialkylphosphate surfactants.

Another surfactant which may be used, preferably used as primary surfactant in combination with other surfactants noted above, is sodium coco glyceryl ether sulfonate. While desirable to use because of its mildness properties, this coco AGS alone does not provide optimum lather creaminess. A sodium 90/10 coconut/tallow alkyl AGS distribution is preferred for creaminess. Salts other than the sodium salt such as TEA-, ammonium, and K-AGS and chain length distributions other than 90/10 coconut/tallow are usable at moderate levels. Also, some soap may be added to improve lather volume and speed of lathering. Certain secondary co-surfactants used in combination with AGS can also provide a creamier and more stable lather. These secondary surfactants should also be intrinsically mild. One secondary surfactant that has been found to be especially desirable is sodium lauroyl sarcosinate (trade name Hamposyl L, made by Hampshire Chemical).

The amphoteric betaines and sultaines noted above can be used as the sole surfactant, but are more preferred as a co-surfactant. Nonionics generally should not be used as the sole surfactant in this product if high foaming is desirable; however, they can be incorporated as a co-surfactant.

Nonionic and cationic surfactants which may be used include any one of those described in U.S. Pat. No. 3,761,418 to Parran, Jr., hereby incorporated by reference into the subject application. Also included are the aldobionamides as taught in U.S. Pat. No. 5,389,279 to Au et al; and the polyhydroxy fatty acid amides as taught in U.S. Pat. No. 5,312,934 to Letton, both of which are incorporated by reference into the subject application.

Soaps may also be used. The soaps may be added neat or made in situ via adding a base, e.g., NaOH; to convert free fatty acids.

A preferred surfactant active system is one such that acyl isethionate comprises 1 to 15% by weight of the total composition and/or an anionic other than acyl isethionate (e.g., ammonium lauryl ether sulfate) comprises 1 to 15% by weight of the total composition and amphoteric comprises 0.5 to 15% by weight of the total composition.

Another preferred active system is one comprising 1 to 20% alkyl ether sulfate. Preferred surfactant systems may also contain 1 to 10% alkali metal lauryl sulfate or $C_{14}$-$C_{16}$ olefin sulphonate instead of acyl isethionate.

Also, in the preferred embodiment, the Hansen solubility parameter of the benefit agent or benefits agents used in combination with the surfactant system should be between 16.5 and 37, preferably 17 and 30, more preferably 19 and 27. When used in a fully formulated composition, the benefit agent(s) will generally comprise 0.1 to 50% by wt., preferably 0.5 to 30%, more preferably 1 to 25% by wt. of the final compositions.

Hansen solubility parameter is the total energy of vaporization of a liquid. This total energies consists of several individual parts arising from (atomic) dispersion forces, (molecular) permanent dipole-permanent dipole forces, and (molecular) hydrogen bonding (electron exchange). The basic equation which governs the assignment of Hansen parameters is that the total cohesion energy, E, must be the sum of the individual energies which make it up.

$$E = E_D + E_P + E_H$$

where $E_D$, $E_P$, $E_H$ are the dispersion cohesion energy, polar cohesion energy and hydrogen bonding cohesion energy, respectively. The Hansen solubility parameter ($\delta$, in unit $MPa^{1/2}$) is thus defined as:

$$\delta^2 = (E_D/V) + (E_P/V) + (E_H/V) = \delta^2_D + \delta^2_P + \delta^2_H$$

where V is the molar volume, and $\delta_D$, $\delta_P$, $\delta_H$ are the Hansen D (dispersion cohesion energy), P (polar cohesion energy) and H (hydrogen bonding cohesion energy).

As noted, the benefit agent may be used in a fully formulated composition in an amount from about, 0.1 to 50% by wt., depending on form of composition.

Examples of oil/solvent or oil/solvent systems having HSP with ranges of invention include alkyl lactate (e.g., butyl lactate), alkyl alcohols (e.g., octyl dodeconol), alcohol such as ethanol, butanol etc.

In a second embodiment of the invention, the invention comprises a method of selecting oil(s)/solvent(s) to be used to reduce surfactant damage in a composition comprising at least one surfactant and benefit agent, wherein said process comprises:

(1) determining Hansen solubility parameter of a benefit agent (e.g., by testing or by finding in literature, and/or by using molecular molding surfactant); and (2) selecting said benefit agent(s) having a Hansen solubility parameter of between 16.5 and 37, preferably 17 and 30, more preferably 19 to 27.

Reduction in surfactant damage may be defined by reduction in number of binding sites binded by surfactant(s) to given protein when surfactant(s) are used in combination with oil/solvent compared to where surfactant alone is used.

Specifically the reduction may be defined in reduction of sites binded of at least about 5%, preferably at least about 10%, more preferably at least about 10% to 50% (and preferably higher) relative to composition without benefit agent or relative to composition with benefit agent outside the defined polarity window.

In a third embodiment, the invention relates to compositions comprising surfactant and a benefit agent or combination of benefit agents having solubility parameter from 16.5 to 37; said composition have reduced surfactant damage. Again, damage is measured by reduction in sites on surfactant binded of at least 5%, preferably at least 10% relative to composition with same surfactant type and amount comprising benefit agent(s) with HSP below 16.5 or above 37, or relative to composition with same type and amount of surfactant and no benefit agent.

Definitions

SDS=Sodium dodecyl sulfate
SLES=Sodium lauryl ether sulfate
CAPB=Cocoamidopropybetaine
CETIOL OE=Dicaprylyl ether
IPM=Isopropylmyristate
Castor oil 318 (also known as Surfactol® 318 from CasChem, Inc. in Bayonne, N.J.) is ethoxylated castor oil with on average 5 PEG unit per castor oil molecule
Castor oil 365 (also known as Surfactol® 365 from CasChem, Inc. in Bayonne, N.J.) is ethoxylated castor oil with on average 40 PEG unit per castor oil molecule
BSA=Bovine serum albumin
HPLC=High performance liquid chromatography
DSC=Differetial Scanning chromatography
B*=The Commission International de l'Eclairage (CIE) L*a*b* color system is used an objective measurement parameter for color. In the 3-dimensional space, L*(luminescence) represents the grey level from black to white, a* represents the green-red component and b* the blue-yellow component.

Methodology/Protocol

Conductivity Test:

Conductance measurements were carried out at room temperature by use of a Thermo conductivity meter, model Orion 150+. Routinely, the titrations were performed by adding a controlled amount of 10% of stock surfactant solution under magnetic stirring into the 0.5% BSA (Bovine Serum Albumin) in 0.02M acetate buffer at pH~5.2. Values of CMC (critical micellization concentration), CAC (critical aggregation concentration) and protein saturation point (PSP) were defined by the changing of the slope of the conductivity vs. surfactant concentration plots. The number of surfactants binding to each protein can be calculated by: $\{[PSP]-[CAC]\}/\{[protein]/Mw_{protein}\}$, where [protein] is the protein concentration.

Indigo Carmine Surfactant/Dye Binding Procedure

A modification of the procedure described by Imokawa and Mishima (*Contact Dermatitis* 5:357-366, 1979) was used. Two mil of each surfactant sample were placed into plastic chambers resting on the volar forearm skin (area~3.14 cm$^2$) for 2 minutes. The samples were removed, and the sites rinsed with 2 mls of deionized water. Two mil of 1% Indigo carmine dye were then added to each chamber for 1 minute and then the sites were rinsed with 2 mil of deionized water. The sites were patted dry with a paper towel. Digital images were obtained for each arm, and each skin site was measured for its L*a*b* values using a Minolta CM 508D. The Commission International de l'Eclairage (CIE) L*a*b* color system is used an objective measurement parameter for color. In the 3-dimensional space, L*(luminescence) represents the grey level from black to white, a* represents the green-red component and b* the blue-yellow component. In this study, each skin site was measured for its L*a*b* values using a Minolta CM 508D spectrophotometer.

The Minolta CM 508D takes three readings on each test site and reports the average. Three sets of average readings were obtained for each site and the values averaged again.

HPLC Test for Surfactant Deposition:

8 weeks old white pig skin was shaved and washed in warm water. Ethanol sprayed and rinse/wiped with wipeall, and then stored it at −7° C. Dose controlled amount of surfactant sample (3.3 mg of per cm$^2$) onto pig skin of known surfactant area. Rub for 30 sec. Let stand for 1.5 min. And then rinse for 10 sec under 100° F. running water. Pat dry and let the skin dry in the hood for around 10 min. Then perform 3 times 1 min extraction using 2 ml mixture solvent (25% chloroform/25% water/50% methanol, by volume) on pig skin for surfactant extraction. Evaporate solvent under liquid $N_2$ and dissolve the content in the vial with 0.5 ml of mobile phase for HPLC analysis using ELSD 2000 detector.

Dynamic Light Scattering for Protein Size:

The size of protein molecule was measured by 90Plus/Bi-MAS multi angle particle size, BrokeHaven. The scattering angle is 90° and the wavelength is 635 nm. 0.5% of protein in acetate buffer (pH=5.2, IS=0.02M) was used. The protein sample was filtered three times by a syringe filter with 0.1 μm pore size Nylon membrane prior to the measurement. All experiments were carried out at room temperature (25° C.). The scattered field autocorrelation function ($g(q, \tau)$) vs. delay time ($\tau$) was obtained from each measurement. A cumulant model was used to fit the autocorrelation function with the delay time to calculate the size of the protein.

Micro—DSC for Protein Denaturation:

1.2% of BSA acetate buffer solution was prepared (pH 5.2, IS 0.02). An accurately measured amount of sample solution was loaded in DSC sample chamber and the thermal behavior of the sample was studied over the range of 5 to 102° C. at a heating rate of 0.5° C./min. Then the BSA acetate solution was titrated with either oil, or surfactant, or oil/surfactant at 1:1 ratio. After each titration, a DSC measurement was performed.

14-Day Cumulative In Vivo Patch Test

A randomized, double-blind study was conducted and consisted of one cell, with 24 subjects 18-65 years of age. Patching occurred for 14 consecutive days, except on Sundays. Patches applied on Saturday were left in place until Monday, when freshly prepared patches were applied. The designated patch test sites were approximately 2 cm×2 cm on the intrascapular area of the back, and approximately 0.2 ml of test product was applied to each patch. Each day following application, the patches were removed, the sites evaluated for irritation, and identical patches reapplied to the same test sites. Monday's irritation scores also were recorded as Sunday's scores, with Sundays being counted as exposure days. Individual test article scores were calculated via summation of the results for each day. Cumulative irritation scores were the sum of the numerical irritation grades assigned daily during the 14-day test period.

EXAMPLE 1-10 & COMPARATIVES A & B

In order to show the effect of benefit agent having different polarity on binding to protein molecule (a reflection of the harshness of surfactant; more surfactant binding to protein equal harsher and more damage expected), applicants tested surfactant binding of (1) surfactant alone and (2) of surfactant in combination with various oils/cosolvents (at 1:1 surfactant to oil ratio) to see level of (how many) surfactants binding per protein molecule (e.g., BSA) at saturation. The tests were done using conductivity test described in protocol and results are set forth below in Table 1.

TABLE 1

Surfactant binding to BSA protein measured by conductivity: 10% SDS with 10% oil compared to 10% SDS alone.

| | Example | Hansen solubility parameter of oil/cosolvent (MPa$^{1/2}$) | Saturated binding: No. of surfactant per BSA at saturation |
|---|---|---|---|
| 10% SDS (surfactant alone) | Control | — | 220 |
| 10% SDS + 10% butyl lactate | 1 | 19.58 | 169 |
| 10% SDS + 10% octyl dodecanol | 2 | 16.98 | 189 |
| 10% SDS + 10% wickenol | 3 | 18.56 | 192 |
| 10% SDS + 10% cetiol OE | 4 | 16.85 | 201 |
| 10% SDS + 10% IPM | A | 16.02 | 237 |
| 10% SDS + 10% dodecane | B | 16.02 | 243 |
| 10% SDS + 10% triolein | 5 | 23.77 | 172 |
| 10% SDS + 10% glycerin | 6 | 36.46 | 202 |
| 10% SDS + 10% methanol | 7 | 29.64 | 188 |
| 10% SDS + 10% ethanol | 8 | 26.49 | 158 |
| 10% SDS + 10% butanol | 9 | 23.28 | 141 |
| 10% SDS + 10% hexanol | 10 | 21.11 | 99 |

As seen, in most cases the number of surfactants binded by BSA went down when oil solvent was added (since surfactant binding is associated with harshness, this is desirable).

On a molecular level, it can be noted that different oils/water soluble solvents have different effect on surfactant binding to protein. Thus, as seen from comparatives A & B (where the Hansen solubility of oil and/or cosolvent was about 16) there was little reduction in number of surfactants binding compared to control with no oil/cosolvent); with other oils/cosolvent there was a mild level of reduction; and with yet other oil/cosolvents (see Example 1 or 5) reduction was quite significant.

Applicants believe there is an optimized polarity window (defined by Hansen solubility parameter of about 16.5 to 37, preferably 17 to 30, more preferably 19 to 27 where most significant reduction is found.

On a macro level, Examples 17-18 and 19 below show that, where polar oil/solvent reduce surfactant binding as measured on a molecular level, surfactant deposition onto skin after wash is also reduced. Therefore, there is a clear link between surfactant binding to protein molecule and surfactant binding to skin during wash.

Figure 6:
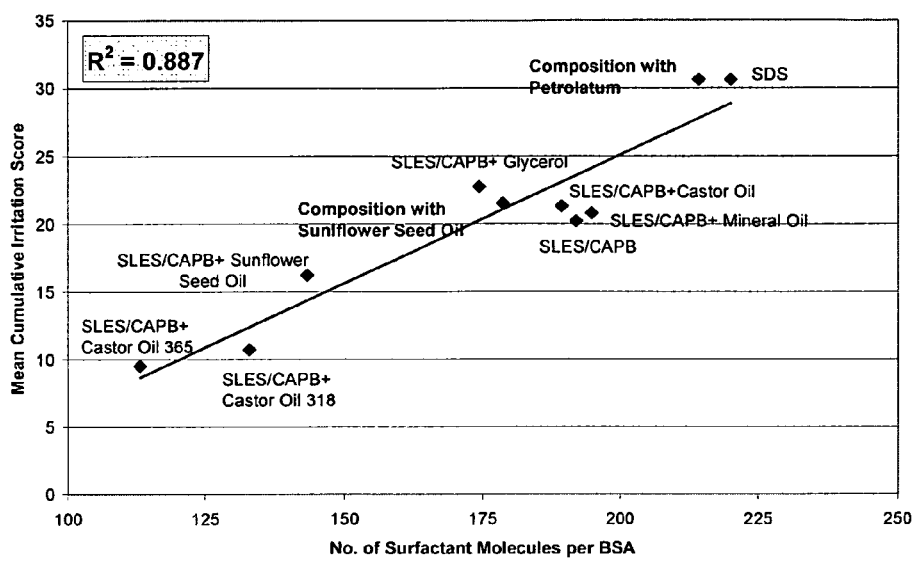
FIG. 6 shows the correlation between the in-vitro surfactant binding to protein and in-vivo skin irritation. As more molecules are binded (e.g., because of HSP outside defined optimal window), mean irritation increases.

Further, in a patch test (see Example 23 and FIG. 6), there is a strong correlation between the irritation score and the surfactant binding to protein in molecular level.

EXAMPLES 11-16

Applicants conducted same test as in Examples 1 to 10, but used SLES/CAPB surfactant system instead of SDS. Results are set forth in Table 2

TABLE 2

Surfactant binding to BSA protein measured by conductivity: 10% SLES/CAPB (2:1) with 10% oil compared to 10% SLES/CAPB (2:1) alone

| | Example | Hansen solubility parameter of oil/cosolvent, (MPa$^{1/2}$) | Saturated binding: No. of surfactant per BSA at saturation |
|---|---|---|---|
| 10% SLES/CAPB (2:1) | Control | — | 183 |
| 10% SLES/CAPB (2:1) + 10% butyl lactate | 11 | 19.58 | 95 |
| 10% SLES/CAPB (2:1) + 10% octyl dodecanol | 12 | 16.98 | 97 |
| 10% SLES/CAPB (2:1) + 10% wickenol | 13 | 18.56 | 145 |
| 10% SLES/CAPB (2:1) + 10% cetiol DE | 14 | 16.85 | 160 |
| 10% SLES/CAPB (2:1) + 10% IPM | C | 16.02 | 165 |
| 10% SLES/CAPB (2:1) + 10% dodecane | D | 16.02 | 192 |
| 10% SLES/CAPB (2:1) + 10% triolein | 15 | 23.77 | 110 |
| 10% SLES/CAPB (2:1) + 10% glycerin | 16 | 36.46 | 150 |

This example, similar to Examples 1-10, is showing that the effect of benefit agent(s) to reduce surfactant binding to protein is dependent on the polarity of the benefit agent: the higher the polarity, the more effective to reduce surfactant binding to protein. There is a window of solubility parameter (from 16.5 to 37, or preferably from 17 to 30, more preferably 19 to 27) that offers the most reduction on surfactant binding to protein.

Importantly, it should be noted is that the choice of oil/solvent to most efficiently reduce surfactant binding to protein is not dependent on surfactant type.

EXAMPLES 17-18

In order to further show the protective effect of benefit agent (e.g., oil), applicants compared surfactant deposition onto skin after wash, using solvent extraction and HPLC method defined in protocol section, for 10% SDS alone and compared with 10% SDS used with dodecane; or used with triolein. Results are seen in FIG. 1 and the amount of SDS deposition on skin after wash is also listed in Table 3 below:

TABLE 3

Surfactant Deposition Onto Pig Skin after Wash Examined by Solvent Extraction After Skin Wash and HPIC

| | Example | SDS deposition on skin (μg/cm$^2$) |
|---|---|---|
| 10% SDS | Control | 17.6 |
| 10% SDS + 10% dodecane | 17 | 15.9 |
| 10% SDS + 10% triolein | 18 | 11.9 |

From FIG. 1 and Table 3, it was found that pig skin washed with SDS has the highest amount of SDS surfactant deposited (17.6+/−1.2 μg/cm2); that pig skin washed with SDS+dodecane (1:1 surfactant to oil ratio) has slightly lower SDS surfactant deposition (15.9+/−0.5 μg/cm$^2$); while pig skin washed with SDS+/31 triolein (1:1 surfactant to oil ratio) has significantly lower SDS surfactant deposition (11.9+/−0.5 μg/cm$^2$). Note that from the in-vitro surfactant binding to protein molecule data shown in Example 1, polar oil such as triolein leads to less surfactant binding to protein on the molecular level than non-polar oil such as dodecane. Therefore, the in-vivo surfactant deposition data and the in-vitro surfactant-protein binding data agree with each other, indicating that polar oil such as triolein will lead to less surfactant binding both on the micro-scale level (surfactant molecule binds to protein molecule) and on the macro-scale level (surfactant binds to skin during wash).

EXAMPLE 19

Figure 2:
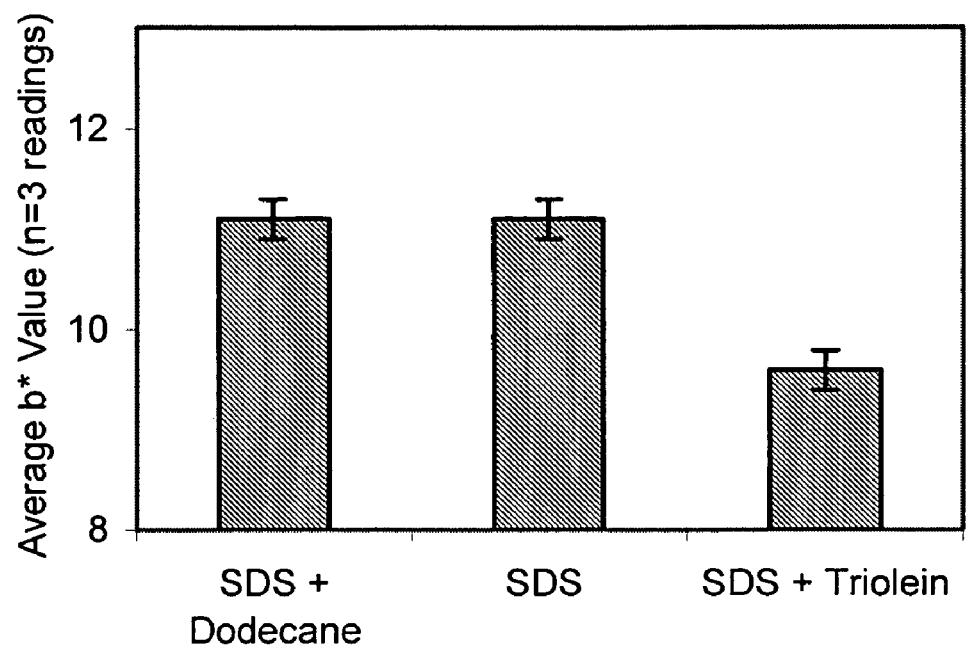
FIG. 2 is a measure of the b* value (defined in protocol). The figure shows that combination of SDS plus triolein (versus SDS plus dodecane or SDS alone) have smaller b* value, which again is indicative of less surfactant binding (associated with less damage).

Applicants again ran a test using SDS versus SDS and dodecane versus SDS and triolein and results are set forth in FIG. 2. Here test measured binding to human forearm during washing (indigo carmine staining test to skin) and 0.5% of each of the three solutions was used to test. A lower b* value indicates less surfactant binding on skin. As shown in FIG. 2, forearm washing with SDS+triolein (a polar oil) shows a lower b* value than SDS alone and SDS+dodecane (a non-polar oil), indicating less surfactant binding to skin after awash. This example once again shows that polar benefit agent (e.g., oil) reduces surfactant binding better than non-polar benefit agent.

EXAMPLE 20

While not wishing to be bound by theory, applicants believe that one mechanism by which benefit agent protects surfactant from denaturation (and exposure to surfactant) is by inducing protein aggregation.

Figure 3:
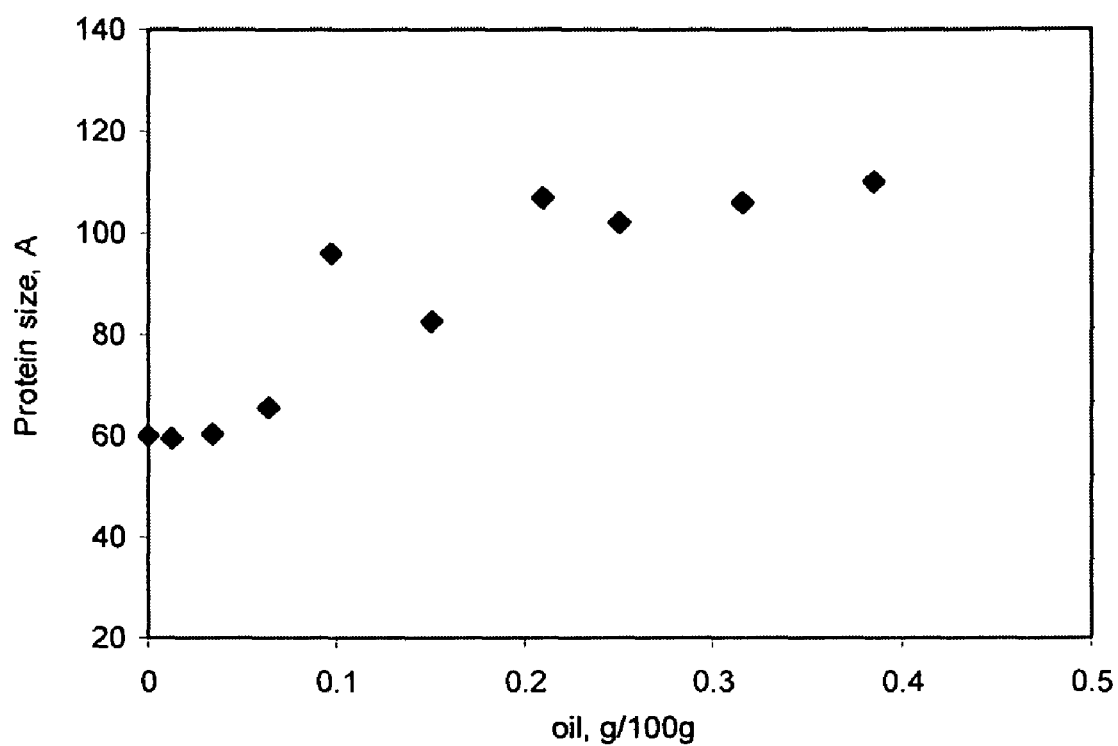
FIG. 3 shows that, as more oil is used, the oil induces aggregation of protein. While not wishing to be bound by theory, protein aggregation is believed to be one of mechanisms by which benefit agent of high polarity (defined by HSP of 16.5 to 37, preferably 17 to 30) protects protein (e.g., from being "attacked" by surfactant(s))

In this regard, applicants measured size of protein (using sunflower seed oil and BSA protein) by dynamic light scattering technique described in protocol section to determine extent of oil induced protein aggregation. As seen from FIG. 3, at roughly 1 to 5 ratio of benefit agent to protein, an increase in protein size was detected by dynamic light scattering thereby indicating aggregation of protein.

EXAMPLE 21

Again, while not wishing to be bound by theory, applicants believe benefit agent (e.g., oil) helps stabilize protein from denaturation (and greater exposure to surfactant) by increasing the heat needed to denature the protein.

Figure 4:
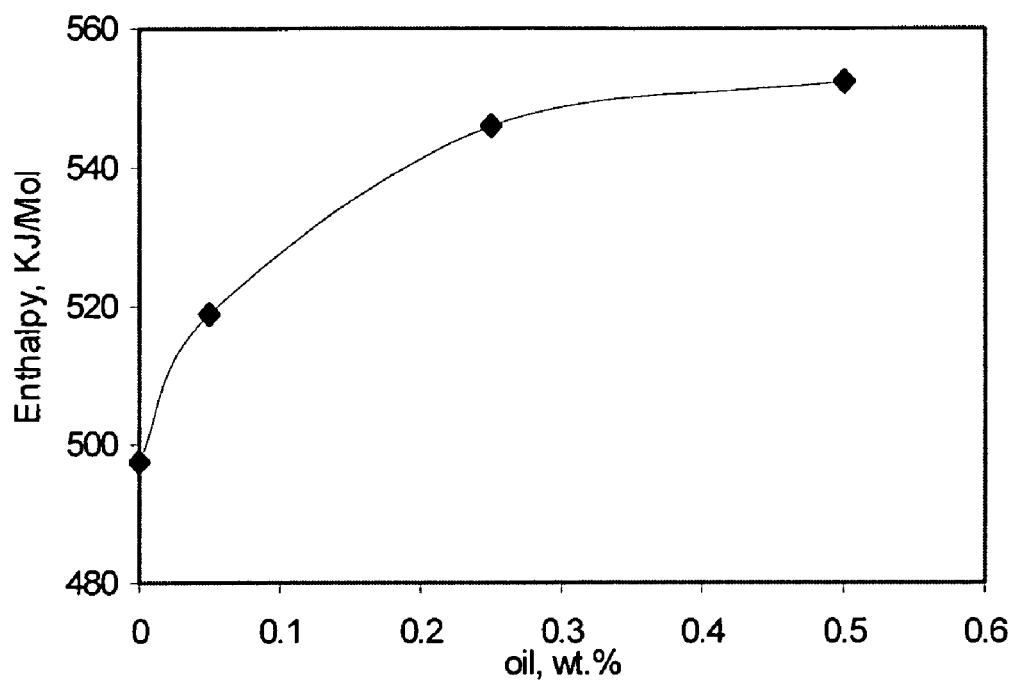
FIG. 4 shows that, as amount of benefit agent is increased, the amount of heat that is needed to denature protein used in combination with the benefit agent is increased. Again, while not wishing to be bound by theory, protection from denaturation is believed to be another mechanism by which benefit agent protects protein from attack by surfactant(s).
Figure 5:
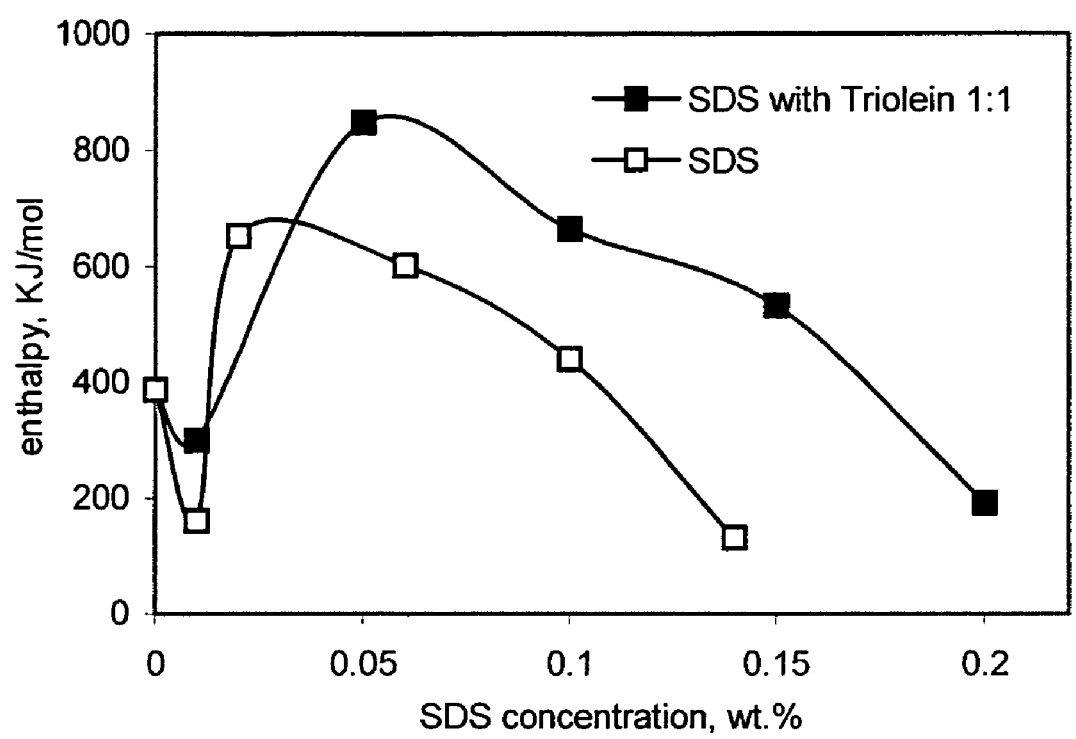
FIG. 5 shows that, without benefit agent of higher polarity (defined by HSP), protein will be denatured by surfactant at much lower temperature than if benefit agent is used.

In this regard, using DSC measurement technique described in methodology section applicants determined that protein alone (BSA) has denaturation enthalpy of about 497 KJ/mol. As indicted in FIG. 4, addition of triolein to the protein solution increases heat needed to achieve denaturation until it reaches a plateau at oil/protein ratio of 1 to 5.

EXAMPLE 22

Again, using DSC data (as shown in FIG. 5), applicants determined that, without benefit agent, SDS willfully denature BSA protein when at room temperature (indicated by denaturation enthalpy approaching zero) at a ratio of about 1.2 to 1 surfactant to protein. However, when there is a 1:1 mixture of SDS triolein, BSA protein is not fully denatured at room temperature until about ratio of 1.8 surfactant to protein. This data clearly indicates that triolein is protecting BSA from surfactant damage.

EXAMPLE 23

In FIG. 6, the in-vitro surfactant binding to protein data was compared to in vivo skin irritation data (measured according to the "14-Day Cumulative In vivo Patch Test" listed in protocol). As shown in FIG. 6, the in vivo data positively correlated with the in vitro findings ($r^2$=0.887) that those polar oils (having higher levels of alkoxylated) lead to less surfactant binding to protein in-vivo also lead to less irritation in-vivo.

The invention claimed is:

1. A method of reducing surfactant damage in compositions comprising at least one anionic surfactant and at least one benefit agent wherein said reduction is measurable by decrease in number of protein binding sites binded by surfactant when benefit agent is present compared to when benefit agent is absent, or compared to when benefit agent used has solubility outside defined range, wherein said method comprises selecting or using said benefit agent or agents having a benefit agent Hansen solubility of 16.5 to 37.

2. A method according to claim 1, wherein benefit agent oil or agents has solubility of 17 to 30.

* * * * *